United States Patent
Lin et al.

(10) Patent No.: US 9,475,705 B2
(45) Date of Patent: Oct. 25, 2016

(54) SELF-BALANCED HIGH-PRESSURE AND HIGH-SHEAR AUTOCLAVE AND THE APPLICATION IN THE PREPARATION OF LAYERED DOUBLE HYDROXIDES

(71) Applicants: Beijing University of Chemical Technology, Beijing (CN); Jiangyin Ruifa Chemical Co., Ltd., Jiangyin, Jiangsu Province (CN)

(72) Inventors: Yanjun Lin, Beijing (CN); Kaitao Li, Beijing (CN); Bo Ning, Beijing (CN); Dianqing Li, Beijing (CN); Xue Duan, Beijing (CN); Chenfa Wen, Jiangyin (CN); Xuchang Tan, Jiangyin (CN)

(73) Assignees: BEIJING UNIVERSITY OF CHEMICAL TECHNOLOGY, Beijing (CN); JIANGYIN RUIFA CHEMICAL CO., LTD., Jiangyin (CN)

( * ) Notice: Subject to any disclaimer, the term of this patent is extended or adjusted under 35 U.S.C. 154(b) by 0 days.

(21) Appl. No.: 14/441,778

(22) PCT Filed: May 21, 2013

(86) PCT No.: PCT/CN2013/075955
§ 371 (c)(1),
(2) Date: Aug. 24, 2015

(87) PCT Pub. No.: WO2014/071726
PCT Pub. Date: May 15, 2014

(65) Prior Publication Data
US 2016/0009566 A1    Jan. 14, 2016

(30) Foreign Application Priority Data

Nov. 9, 2012  (CN) .......................... 2012 1 0445903

(51) Int. Cl.
| | | |
|---|---|---|
| C01G 9/02 | (2006.01) |
| C01F 7/00 | (2006.01) |
| C07F 15/04 | (2006.01) |
| B01J 19/18 | (2006.01) |
| C01B 13/36 | (2006.01) |
| C01G 53/00 | (2006.01) |
| C01G 9/00 | (2006.01) |
| B01J 8/20 | (2006.01) |
| B01J 8/22 | (2006.01) |
| B01J 8/00 | (2006.01) |
| B01F 7/16 | (2006.01) |

(52) U.S. Cl.
CPC ............... *C01G 9/02* (2013.01); *B01J 8/0005* (2013.01); *B01J 8/006* (2013.01); *B01J 8/20* (2013.01); *B01J 8/222* (2013.01); *B01J 19/18* (2013.01); *C01B 13/366* (2013.01); *C01F 7/004* (2013.01); *C01F 7/005* (2013.01); *C01G 9/006* (2013.01); *C01G 53/006* (2013.01); *C07F 15/04* (2013.01); *B01F 7/1635* (2013.01); *B01J 2208/00106* (2013.01); *B01J 2208/00867* (2013.01); *B01J 2219/185* (2013.01); *C01P 2002/22* (2013.01); *C01P 2002/72* (2013.01); *C01P 2004/03* (2013.01); *C01P 2004/20* (2013.01); *C01P 2004/50* (2013.01); *C01P 2004/52* (2013.01); *C01P 2004/61* (2013.01); *C01P 2004/62* (2013.01)

(58) Field of Classification Search
CPC ...... C01G 53/006; C01G 9/02; C01G 9/006; C07F 15/04; C01B 13/366; C01F 7/005; C01F 7/004; B01J 19/18; C01P 2004/03; C01P 2004/20; C01P 2004/50; C01P 2004/61; C01P 2004/62; C01P 2002/72; C01P 2002/22; C01P 2004/52
USPC .......................... 423/420.2; 422/226; 556/31
See application file for complete search history.

(56) References Cited

U.S. PATENT DOCUMENTS

| | | |
|---|---|---|
| 2008/0170978 A1 | 7/2008 | Duan et al. |
| 2009/0202427 A1 | 8/2009 | Katusic et al. |
| 2016/0009566 A1* | 1/2016 | Lin ...................... C01G 53/006 423/420.2 |

FOREIGN PATENT DOCUMENTS

| | | |
|---|---|---|
| CN | 1146653 | 4/1997 |
| CN | 1994888 | 7/2007 |
| CN | 101798064 | 8/2010 |
| CN | 102897717 | 1/2013 |
| CN | 102908967 | 2/2013 |

OTHER PUBLICATIONS

Machine Translation of CN101798064A.*
International Search Report issued in PCT International Application No. PCT/CN2013/075955, mailed Aug. 29, 2013, 6 pages.

* cited by examiner

*Primary Examiner* — Daniel C McCracken
(74) *Attorney, Agent, or Firm* — Hamre, Schumann, Mueller & Larson, P.C.

(57) ABSTRACT

The present invention belongs to the synthesis technology field of inorganic functional materials, and particularly provides a self-balanced high-pressure and high-shear autoclave and its application in the preparation of layered double hydroxides (LDHs). In this invention, by imbedding the handpiece of emulsification mill into the autoclave, and by taking the motor driving system outside of the autoclave, the pressure of the autoclave can be highly stable by the use of self-balanced seal gland. These characters solve the problem that the typical emulsification mill cannot be used in high-pressure system, and ensure the crystallization under the high-pressure and high-shear conditions. Such autoclave takes the advantages of additional equipment, and eliminates the volume effect in the amplification process. By the use of this new autoclave, the reaction time can be shorten from 24 hours to 2-6 hours, the reaction temperature can be reduced from 180° C. to 140° C. The LDHs products with small particle size and narrow size distribution are obtained. These results are better than those prepared at the laboratory level.

9 Claims, 2 Drawing Sheets

SELF-BALANCED HIGH-PRESSURE AND HIGH-SHEAR AUTOCLAVE AND THE APPLICATION IN THE PREPARATION OF LAYERED DOUBLE HYDROXIDES

FIELD OF THE INVENTION

The present invention belongs to the synthesis technology field of inorganic functional materials, and particularly provides a self-balanced high-pressure and high-shear autoclave and its application in the preparation of layered double hydroxides (LDHs).

BACKGROUND OF THE INVENTION

Layered double hydroxides (LDHs), also known as hydrotalcite, are one type of anionic layered materials. The general formula can be described as: $[M^{2+}_{1-x}M^{3+}_x(OH)_2]A^{n-}_{x/n}\cdot mH_2O$, in which the $M^{2+}$ and $M^{3+}$ are divalent and trivalent metal ions, respectively; $A^{n-}$ is an anion. x is the molar fraction of $M^{3+}$; m is the numbers of crystalline water. The chemical elements, compositions and ratios of the host layers, and the types and numbers of the interlayer guests can be tuned in a wide range, and thus a series of new materials with specific structures and properties can be obtained.

The previous patent (No. CN1994888A) has put forwards a new method for the preparation of LDHs in a clean way. In this method, bruciteis used as the raw material that is rich in China. The LDHs are synthesized under high-temperate hydrothermal condition by mixing the brucite with aluminum hydroxide. Based on the reaction mechanism, brucite can dissolve into $Mg^{2+}$ ions under high temperature condition, and form the nucleation at the surface of the aluminum hydroxide. The as-used autoclave is the common paddle-like stirring reactor, which cannot remove the nucleation from the surface of the aluminum hydroxide. The nucleus thus has hindered the continuous reaction, and reduced the reaction rate and yield. The obtained LDHs particles usually present a large size and wide distribution. These disadvantages have largely restricted the applications of LDH materials.

SUMMARY OF THE INVENTION

To accelerate the reaction rate and to obtain the LDHs products with high purity, small size and narrow size distribution, this patent supplies a self-balanced high-pressure and high-shear autoclave and its application in the preparation of LDHs.

The technology scheme involves: injecting the mixture of hydroxides into the sand mill for the reduction of particle sizes, and then transferring into the self-balanced high-pressure and high-shear autoclave under high temperature; introducing the $CO_2$ or acid $H_nA^n$. After the reaction, the slurry can be filtrated and dried directly to obtain the LDHs products.

The characters of the as-described self-balanced high-pressure and high-shear autoclave are as follows: 1. The handpiece of emulsification mill is placed inside the autoclave; 2. the top of the auto clave is self-balanced seal gland, which is composed by the self-propelled surge tank with a isolation-type piston and sealing layer; 3. the coupling shaft of the high-shear emulsification mill can get into the autoclave through seal gland; 4. the bottom of the coupling shaft connect the handpiece, which is away from the bottom of the autoclave with 1/5-1/2 of the whole height; 5. the top of the coupling shaft connect the motor driving system, which is located outside of the autoclave; 6. the coupling shaft is based on sleeve, the outer shaft is based on the connection of dead axis and stator in handpiece, and the inner shaft is based on the connection of rotation axis and rotor in handpiece.

The characters of the as-described self-propelled surge tank are as follows: 1. the connection tube at the bottom of the tank can inlet into the autoclave, and the connection tube on the top of the tank can connect with the sealing layer; 2. upon increasing the pressure of the autoclave, the piston rises, and the sealing liquid in the tank can move into the sealing layer, resulting in a balanced pressure with inner autoclave.

The as-described self-balanced high-pressure and high-shear autoclave can be used in the preparation of LDHs, and detailed processes are described as follows:

A. Mixing the hydroxides of $M^{2+}$ and $M^{3+}$ with the molar ratio of 1-4, and adding the deionized water into the mixture, where the total amount of water is 0.25~999 fold of the hydroxides. With the pre-treatment of the sand mill, the mixture can be transferred into the self-balanced high-pressure and high-shear autoclave.

B. Under 100-300° C., the high-shear emulsification mill can be operated, the shear rate is set at 500-3000 rpm, the rate of the pumping $CO_2$ is set at 0.1-1000 ml/min (or the ratio of the adding acid $H_nA^n$ is set at $M^{3+}/A^{n-}$=n). After 0.1-3 days, the slurry can be filtrated and dried directly. The LDHs with $CO_3^{2-}$ or $A^{n-}$ located in the interlayer can be obtained.

$M^{2+}$ is divalent cation, which can be one or two types of $Mg^{2+}$, $Zn^{2+}$, $Ca^{2+}$, $Cu^{2+}$, $Ni^{2+}$, $Co^{2+}$, $Fe^{2+}$, $Mn^{2+}$ and $Be^{2+}$; preferentially, $M^{2+}$ can be one or two types of $Mg^{2+}$, $Zn^{2+}$, $Ca^{2+}$ and $Ni^{2+}$; $M^{3+}$ is trivalent cation, which can be one or two types of $Al^{3+}$, $Ni^{3+}$, $Co^{3+}$, $Fe^{3+}$, $Mn^{3+}$, $Cr^{3+}$, $V^{3+}$, $Ti^{3+}$, $In^{3+}$ and $Ga^{3+}$; preferentially, $M^{3+}$ can beone or two types of $Al^{3+}$, $Ni^{3+}$, $Fe^{3+}$.

Acid anion ($A^{n-}$) can be one or more types of ions as follows: (1) inorganic anions: $F^-$, $Cl^-$, $Br^-$, $I^-$, $NO_3^-$, $ClO_3^-$, $ClO_4^-$, $IO_3^-$, $H_2PO_4^-$, $CO_3^{2-}$, $SO_3^{2-}$, $S_2O_3^{2-}$, $HPO_4^-$, $WO_4^{2-}$, $CrO_4^{2-}$, $PO_4^{3-}$; (2) organic anions: terephthalate, adipate, succinate, twelve alkyl sulfonate, p-hydroxybenzoate, benzoate; (3) isopoly acid and heteropoly acid anions: $Mo_7O_{24}^{6-}$, $V_{10}O_{28}^{6-}$, $PW_{11}CuO_{39}^{6-}$, $SiW_9W_3O_{40}^{7-}$; preferentially, $A^{n-}$ is one type of $Cl^-$, $NO_3^-$, $CO_3^{2-}$, $SO_3^{2-}$, $PO_4^{3-}$, terephthalate, succinate, benzoate or $Mo_7O_{24}^{6-}$; n is valence state of the anion, and n=1-7.

In step B: the pumped $CO_2$ can be replaced by dry ice, and the molar ratio of dry ice to $M^{3+}$ is 0.5-20.

Advantageous effects: The nucleation of $Mg^{2+}$ occurs at the surface of the aluminum hydroxide after dissolving of the brucite during the clean process of LDHs, which will influence the continuous reaction. Based on these facts, this innovation has designed a self-balanced high-pressure and high-shear autoclave. In this autoclave, the handpiece of emulsification mill is imbedded into the autoclave, and the motor driving system is set outside of the autoclave. The pressure of the autoclave can be highly stable by the use of self-balanced seal gland. These characters solve the problem that the typical emulsification mill cannot be used in high-pressure system, and ensure the crystallization can be performed under the high-pressure and high-shear conditions. Such autoclave takes the advantages of additional equipment, and eliminates the volume effect in the amplification process. By the use of this new autoclave, the reaction time can be shorten from 24 hours to 2-6 hours, the reaction temperature can be reduced from 180° C. to 140° C. The initial particle size of the LDHs products is reduced from 5-10 μm to 0.5-2 μm, and the aggregate particle size of the LDHs products ($d_{90}$) is less than 3 um. Therefore, the LDHs products with small particle size and narrow distribution are obtained, which are better than those prepared at the laboratory level.

DETAILED DESCRIPTION OF THE EMBODIMENTS

The present invention will be further explained through following examples:

Example 1

A: Mixing $Mg(OH)_2$ and $Al(OH)_3$ with the molar ratio of $Mg^{2+}/Al^{3+}=2:1$, and adding 9 kg of deionized water into the 1 kg of hydroxide mixture. With the pre-treatment of the sand mill, the mixture can be transferred into the self-balanced high-pressure and high-shear autoclave;

B. Operating the high-shear emulsification mill with the shear rate at 1000 rpm, the temperature is increased to 120° C., and the pumping rate of $CO_2$ is set at 1 L/min. After 6 hours, the slurry can be filtrated and dried at 70° C. for 8 hours. The LDHs with the molecular formula $Mg_4Al_2(OH)_{12}CO_3.4H_2O$ can be obtained.

Figure 1:
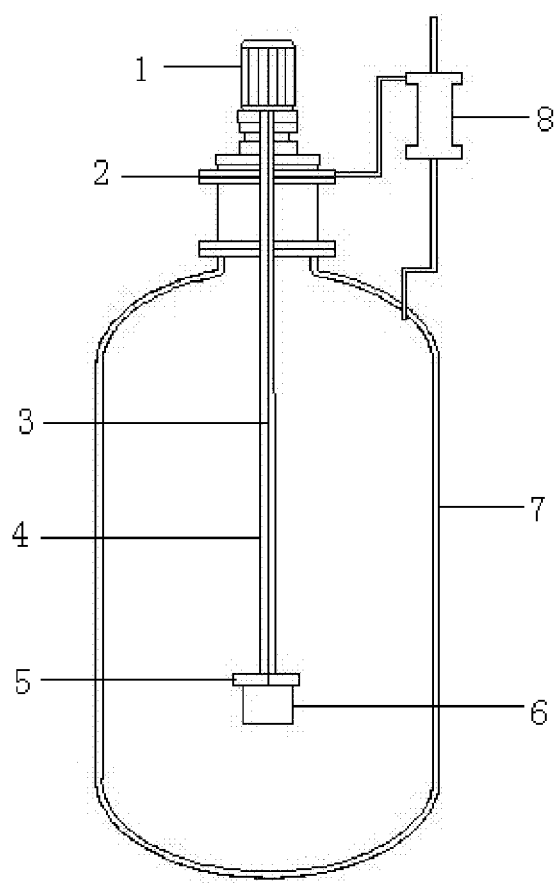
FIG. 1: the structural scheme of the self-balanced high-pressure and high-shear autoclave: 1—motor driving system, 2—sealing layer, 3—rotation shaft, 4—dead axle, 5—stator of the handpiece, 6—rotor of the handpiece, 7—autoclave, 8—self-propelled surge tank with a isolation-type piston.

The characters of the as-described self-balanced high-pressure and high-shear autoclave (shown in FIG. 1) are as follows: 1. the handpiece of emulsification mill is placed into the autoclave; 2. the top of the autoclave is self-balanced seal gland, which is composed by the self-propelled surge tank with an isolation-type piston and sealing layer; 3. the coupling shaft of the high-shear emulsification mill can get into the autoclave through seal gland; 4. the bottom of the coupling shaft connect the handpiece, which is away from the bottom of the autoclave with ⅓ of the whole height; 5. the top of the coupling shaft connect the motor driving system, which is located outside of the autoclave; 6. the coupling shaft is based on sleeve, the outer shaft is based on the connection of dead axis and stator in handpiece, and the inner shaft is based on the connection of rotation axis and rotor in handpiece.

The characters of the as-described self-propelled surge tank are as follows: 1. the connection tube at the bottom of the tank can inlet into the autoclave, and the connection tube on the top of the tank can connect with the sealing layer; 2. upon increasing the pressure of the autoclave, the piston rises, and the sealing liquid in the tank can move into the sealing layer, resulting in a balanced pressure with inner autoclave; the sealing liquid is hydraulic oil.

Figure 2:
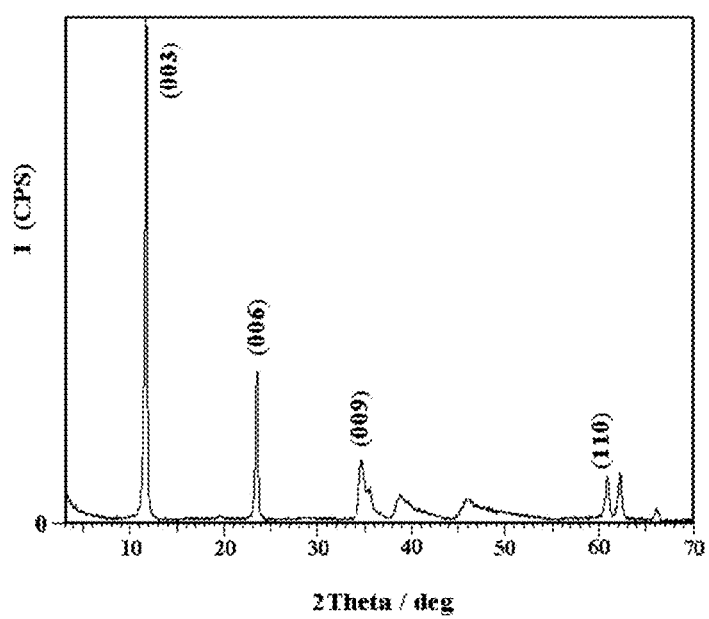
FIG. 2: XRD patterns of the obtained LDHs.

The XRD of the LDHs samples were characterized on an X-ray diffracto meter (XRD-6000, SHIMADZU, Japan). As shown in FIG. 2, the characteristic peaks of $Mg_2Al$—$CO_3$-LDHs appear at $2\theta=11.7°, 23.4°, 34.5°$ and $60.8°$. The sharp peaks confirm the high crystalline degree.

Figure 3:
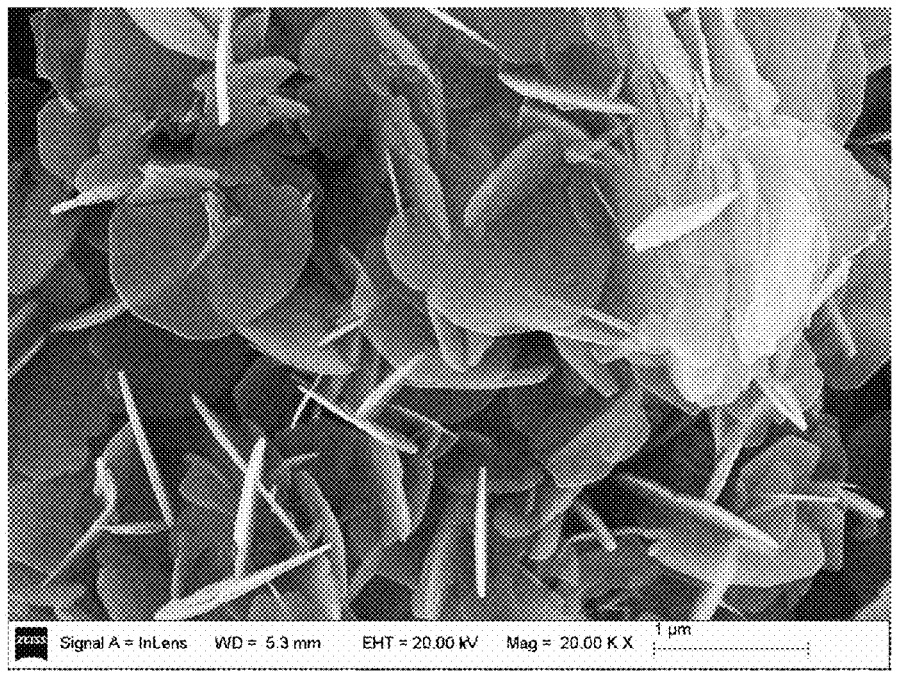
FIG. 3: SEM images of the obtained LDHs.

Scanning electron microscopy (SEM) images were obtained using a ZEISS (Germany) scanning electron microscope, and the particle size and morphology can be obtained as shown in FIG. 3. The particle size is ca. 1 um.

Figure 4:
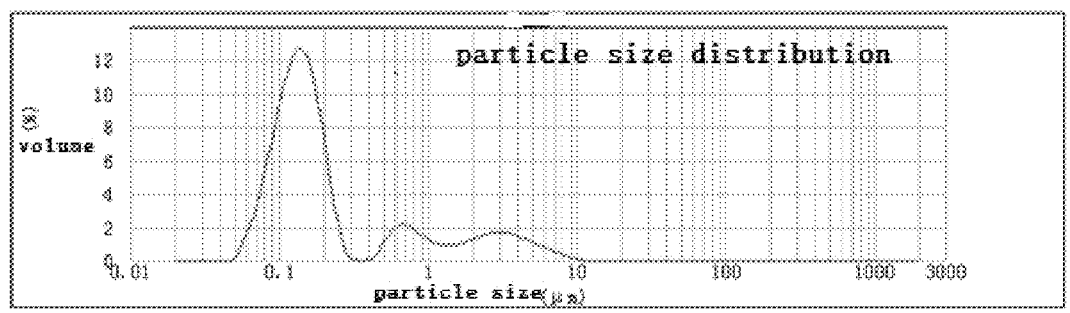
FIG. 4: Particle size distribution of the obtained LDHs.

The particle size was also detected by the Mastersizer2000 laser particle size analyzer (UK). FIG. 4 shows the laser particle size distribution with the average aggregate particle size of 0.14 um and $d_{90}=2.3$ um.

Example 2

A: Mixing $Zn(OH)_2$, $Mg(OH)_2$ and $Al(OH)_3$ with the molar ratio of $Zn^{2+}/Mg^{2+}/Al^{3+}=1:3:2$, and adding 8 kg of deionized water into 2 kg of hydroxide mixture. With the pre-treatment of the sand mill, the mixture can be transferred into the self-balanced high-pressure and high-shear autoclave.

B. Adding 4 kg of dry ice into the high-shear emulsification mill with the shear rate at 1500 rpm, the temperature is increased to 140° C. After 4 hours, the slurry can be filtrated and dried at 70° C. for 8 hours. The LDHs with the molecular formula $ZnMg_3Al_2(OH)_{12}CO_3.4H_2O$ can be obtained.

Example 3

A: Mixing $Mg(OH)_2$ and $Al(OH)_3$ with the molar ratio of $Mg^{2+}/Al^{3+}=3:1$, and adding 9 kg of deionized water into 1 kg of hydroxide mixture. With the pre-treatment of the sand mill, the mixture can be transferred into the self-balanced high-pressure and high-shear autoclave.

B. Operating the high-shear emulsification mill with the shear rate at 1500 rpm, the temperature is increased to 140° C., and the pumping rate of $CO_2$ is set at 1 L/min. After 6 hours, the slurry can be filtrated and dried at 70° C. for 8 hours. The LDHs with the molecular formula $Mg_6Al_2(OH)_{16}CO_3.4H_2O$ can be obtained.

Example 4

A: Mixing $Ni(OH)_2$ and $Fe(OH)_3$ with the molar ratio of $Ni^{2+}/Fe^{3+}=4:1$, and adding 9 kg of deionized water into the 500 g of hydroxide mixture. With the pre-treatment of the sand mill, the mixture can be transferred into the self-balanced high-pressure and high-shear autoclave.

B: Adding 58 g of terephthalic acid into the high-shear emulsification mill with the shear rate at 2000 rpm, the temperature is increased to 100° C. After 5 hours, the slurry can be filtrated and dried at 70° C. for 8 hours. The LDHs with the molecular formula $Ni_8Fe_2(OH)_{20}(C_8H_4O_4).4H_2O$ can be obtained.

Example 5

A: Mixing $Zn(OH)_2$, $Mg(OH)_2$ and $Al(OH)_3$ with the molar ratio of $Zn^{2+}/Mg^{2+}/Al^{3+}=1:1:1$, and adding 8.5 kg of deionized water into 1.5 kg of hydroxide mixture. With the pre-treatment of the sand mill, the mixture can be transferred into the self-balanced high-pressure and high-shear autoclave.

B. Adding 4 kg of dry ice into the high-shear emulsification mill with the shear rate at 2000 rpm, the temperature is increased to 140° C. After 6 hours, the slurry can be filtrated and dried at 70° C. for 8 hours. The LDHs with the molecular formula $ZnMg_3Al_2(OH)_{12}CO_3.4H_2O$ can be obtained.

The invention claimed is:

1. A self-balanced high-pressure and high-shear apparatus, comprising:
an autoclave;
a self-balanced seal gland including a self-propelled surge tank, a piston and a sealing layer, and
a high-shear emulsification mill including a handpiece, a coupling shaft, and a motor driving system,
wherein the self-balanced seal gland is disposed on a top of the autoclave,
wherein the handpiece includes a stator and a rotor, the handpiece is disposed inside the autoclave, the coupling shaft extends into the autoclave through the sealing layer, the coupling shaft has a first end and a second end opposing the first end, the first end is located inside the autoclave and the second end is located outside the autoclave, the first end of the coupling shaft is connected to the handpiece, the handpiece is $1/5$-$1/2$ of the whole height of the autoclave from the bottom of the autoclave, the second end of the coupling shaft is connected to the motor driving system, the motor driving system is disposed outside the autoclave, and
wherein the coupling shaft includes an outer shaft and an inner shaft, the outer shaft is a dead axle and connected to the stator of the handpiece, the inner shaft is a rotation axle and connected to the rotor of the handpiece.

2. The apparatus of claim 1, wherein the self-propelled surge tank contains a sealing liquid and has a first tube disposed at a bottom thereof and a second tube disposed at a top thereof, the first tube is in connection with the autoclave, the second tube is in connection with the sealing layer, the piston allows moving the sealing liquid into the sealing layer upon increasing a pressure in the autoclave to balance pressures of the autoclave and the sealing layer.

3. A method of preparing a layered double hydroxide product using the self-balanced high-pressure and high-shear apparatus of claim 1, comprising
mixing $M^{2+}$ and $M^{3+}$ hydroxides in a $M^{2+}/M^{3+}$ molar ratio of 1-4 to form a first mixture;
obtaining a second mixture by adding deionized water into the first mixture in a total amount being 0.25~999 fold of total mass of the $M^{2+}$ and $M^{3+}$ hydroxides;
treating the second mixture using a sand mill to form a third mixture and transferring the third mixture to the self-balanced high-pressure and high-shear apparatus of claim 1;
operating a high-shear emulsification mill at a shear rate of 500-3000 rpm, pumping $CO_2$ at a rate of 0.1-1000 ml/min or adding acid $H_nA^{n-}$ to obtain a slurry, where $A^{n-}$ is an anion and n=1-7;
filtrating and drying the slurry after 0.1-3 days of operating the high-shear emulsification mill; and
obtaining a layered double hydroxide product with $CO_3^{2-}$ or $A^{n-}$ located in an interlayer.

4. The method of claim 3, wherein the $M^{2+}$ is a divalent cation, the $M^{2+}$ is one or two selected from $Mg^{2+}$, $Zn^{2+}$, $Ca^{2+}$, $Cu^{2+}$, $Ni^{2+}$,
the $M^{3+}$ is a trivalent cation, the $M^{3+}$ is one or two selected from $Al^{3+}$, $Ni^{3+}$, $Co^{3+}$, $Fe^{3+}$, $Mn^{3+}$, $Cr^{3+}$, $V^{3+}$, $Ti^{3+}$, $In^{3+}$ and $Ga^{3+}$.

5. The method of claim 3, wherein the $A^{n-}$ is one or two types of ions selected from: (1) inorganic anions including $F^-$, $Cl^-$, $Br^-$, $I^-$, $NO_3^-$, $ClO_3^-$, $ClO_4^-$, $IO_3^-$, $H_2PO_4^-$, $CO_3^{2-}$, $SO_3^{2-}$, $S_2O_3^{2-}$, $HPO_4^{2-}$, $WO_4^{2-}$, $CrO_4^{2-}$, and $PO_4^{3-}$; (2) organic anions including terephthalate, adipate, succinate, twelve alkyl sulfonate, p-hydroxybenzoate, and benzoate; and (3) isopoly acid and heteropoly acid anions including $Mo_7O_{24}^{6-}$, $V_{10}O_{28}^{6-}$, $PW_{11}CuO_{39}^{6-}$, and $SiW_9W_3O_{40}^{7-}$.

6. A method to prepare a layered double hydroxide product using the self-balanced high-pressure and high-shear apparatus of claim 1, comprising:
mixing $M^{2+}$ and $M^{3+}$ hydroxides in a $M^{2+}/M^{3+}$ molar ratio of 1-4 to form a first mixture, where the $M^{2+}$ is a divalent cation and the $M^{3+}$ is a trivalent cation;
adding deionized water into the first mixture to obtain a second mixture, the total amount of water being 0.25~999 fold of the total mass of the $M^{2+}$ and $M^{3+}$ hydroxides;
treating the second mixture using a sand mill to form a third mixture and transferring the third mixture to the self-balanced high-pressure and high-shear apparatus of claim 1;
operating a high-shear emulsification mill at a shear rate of 500-3000 rpm, adding dry ice in the autoclave in a dry ice-to-$M^{3+}$ molar ratio of 0.5-20 to obtain a slurry;
filtrating and drying the slurry after 0.1-3 days of operating the high-shear emulsification mill; and
obtaining a layered double hydroxide product,
wherein the $M^{2+}$ is one or two selected from $Mg^{2+}$, $ZN^{2+}$, $Ca^{2+}$, $Cu^{2+}$, $Ni^{2+}$, $Co^{2+}$, $Fe^{2+}$, $Mn^{2+}$, $Cd^{2+}$ and $Be^{2+}$, and
the $M^{3+}$ is one or two selected from $Al^{3+}$, $Ni^{3+}$, $Co^{3+}$, $Fe^{3+}$, $Mn^{3+}$, $Cr^{3+}$, $V^3+$, $Ti^{3+}$, $In^{3+}$ and $Ga^{3+}$.

7. The method of claim 4, wherein the $M^{2+}$ is one or two selected from $Mg^{2+}$, $Zn^{2+}$, $Ca^{2+}$, and $Ni^{2+}$.

8. The method of claim 4, wherein the $M^{3+}$ is one or two selected from $Al^{3+}$, $Ni^{3+}$, and $Fe^{3+}$.

9. The method of claim 5, wherein the $A^{n-}$ is one selected from $Cl^-$, $NO_3^-$, $CO_3^{2-}$, $SO_3^{2-}$, $PO_4^{3-}$, terephthalate, succinate, benzoate, and $Mo_7O_{24}^{6-}$.

* * * * *

UNITED STATES PATENT AND TRADEMARK OFFICE
CERTIFICATE OF CORRECTION

PATENT NO. : 9,475,705 B2
APPLICATION NO. : 14/441778
DATED : October 25, 2016
INVENTOR(S) : Lin et al.

It is certified that error appears in the above-identified patent and that said Letters Patent is hereby corrected as shown below:

On the Title Page

Item (73), after "Assignees:", delete:
"JIANGYIN RUIFA CHEMICAL CO., LTD., Jiangyin, Jiangsu Province (CN)"

Signed and Sealed this
Twenty-sixth Day of June, 2018

Andrei Iancu
*Director of the United States Patent and Trademark Office*